US00PP09839P

United States Patent [19]

Drewlow

[11] Patent Number: Plant 9,839

[45] Date of Patent: Mar. 25, 1997

[54] KALANCHOE PLANT NAMED EMPRESS

[75] Inventor: Lyndon W. Drewlow, Ashtabula, Ohio

[73] Assignee: Mikkelsens, Inc., Ashtabula, Ohio

[21] Appl. No.: 489,715

[22] Filed: Jun. 13, 1995

[51] Int. Cl.[6] ..... A01H 5/00

[52] U.S. Cl. ..... Plt./87.15

[58] Field of Search ..... Plt./87.15

[56] References Cited

U.S. PATENT DOCUMENTS

P.P. 4,344 12/1978 Hope ..... Plt./87.15

P.P. 4,345 12/1978 Hope ..... Plt./87.15

*Primary Examiner*—James R. Feyrer

*Attorney, Agent, or Firm*—Foley & Lardner

[57] ABSTRACT

A new Kalanchoe cultivar named Empress characterized by the combined features of cherry red flower color, excellent basal branching, early flowering time, relatively compact plant habit, floriferous habit, and excellent keeping quality.

1 Drawing Sheet

The present invention relates to a new and distinct cultivar of Kalanchoe plant, botanically known as *Kalanchoe blossfeldiana,* and known by the cultivar name Empress.

Empress was developed by the inventor Lyndon W. Drewlow in a controlled breeding program in Ashtabula, Ohio. The female or seed parent was Mikkelsen Seedling No. 90-298-1 and the male or pollen parent was 88-499-1.

Asexual reproduction by stem cuttings taken by the inventor in Ashtabula, Ohio has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry. The characteristics are described with comparative reference to the cultivars Cherry Jubilee (U.S. Pat. No. P.P. 5,877), Legacy (U.S. Pat. No. P.P. 9,111).

1. Empress has cherry red flowers which open 53B to 53C (R.H.S.) and fade to 67B, while Cherry Jubilee has much redder flowers at opening (44B) which fade to 58C, a duller color. The flowers of Legacy are lilac (71C to 71D) in color.

2. Empress has smaller leaves (6 to 7 cm long and 4 to 5 cm wide) than Legacy (7 to 8 cm long and 5 to 6 cm wide) and Cherry Jubilee (8 to 9 cm long and 5 to 6 cm wide).

3. Both Empress and Legacy have excellent basal branching starting with the nodes at the soil line in the pot, while Cherry Jubilee does not break well from the bottom 2 or 3 nodes.

4. Both Empress and Legacy have mounded growth habits, with flowers on the upper two-thirds of the plant of Empress. Empress is 12 to 15 cm high and 22 to 25 cm wide while Cherry Jubilee is more upright, being 18 to 20 cm high and 20 to 22 cm wide, with flowers the on upper one-half of the plant.

5. Empress and Legacy have similar sized flowers at 14 to 15 mm in diameter, while Cherry Jubilee has a larger flower (16 to 17 mm in diameter).

6. Empress is 7 to 10 days earlier to bloom under winter growing conditions compared to Cherry Jubilee, but is similar to Legacy.

7. When mature, both Empress and Legacy have stigmatic surfaces that are white in color while Cherry Jubilee has pinkish white mature stigmas.

8. Empress has better keeping quality than Cherry Jubilee, with flowers keeping up to a week longer. In addition, Empress has no foliar yellowing of the leaf margins.

9. Pedicels on terminal and lateral branches of Empress are 5 to 7 mm shorter than on Cherry Jubilee if comparable pedicel positions are compared. Legacy is similar in this trait to Empress.

The accompanying color photograph is a top perspective view of Empress, illustrating the colors as true as it is reasonably possible to obtain in a color reproduction of this type. The photograph was taken on Mar. 31, 1995, under natural light on an overcast day under a ridged plastic covering at Ashtabula, Ohio.

The following is a detailed description of the new cultivar, based on plants produced in greenhouses in Ashtabula, Ohio during the winter season of the year. Plants were grown in 10 cm pots and measurements were taken 16 weeks after rooted cuttings were planted. Height measurements were taken from the soil line of the container. The plants were grown at 65° to 68° F. night temperatures, 3500 to 4000 foot candles of light, and nutritional levels of 175 ppm Nitrogen, 50 ppm Potassium, and 175 PPM Phosphorous, with trace elements added. Habit of growth, plant height, flowering time, size of leaves and peduncle length will be influenced by nutritional and environmental conditions.

Color references are made to The Royal Horticultural Society Colour Chart except where general terms of ordinary dictionary significance are used.

Classification:

*Commercial.*—*Kalanchoe blossfeldiana* cv. Empress.

Parentage: A controlled cross between female parent Mikkelsen Seedling No. 90-298-1 and male parent Mikkelsen Seedling No. 88-499-1.

Propagation:

*Type cutting.*—Stem tip cutting up to 3 cm long.

*Time to root.*—10 days at 21° C. summer; 14 days at 21° C. winter.

*Rooting habit.*—Fine, fibrous, abundant.

Plant description:

*Habit and form of growth.*—Compact, semi-mounded; excellent basal branching, flower clusters bloom above foliage. Environment and use of growth regulators will play a role in final height.

*Foliage.*—Leaves are simple and opposite. Size: Average full grown leaves on a plant when grown in a 10 cm pot are 6 to 7 cm long and 4.5 to 5.0 cm wide. Shape: Ovate, apex obtuse, base acute to rounded. Texture: Glabrous, coriaceous and succulent. Margin: Crenate, shallow lobed. Color: Young foliage, top side 146B, under side 146C; mature foliage, top side 147A, under side between 147A and 147B.

Flowering description:

*Flowering habits.*—Inflorescence is a compound dichasial cyme. Terminal flower on main axis opens first followed by the terminal flowers of the side branches, continuing with the subsequent development of branches in the inflorescence. Inflorescence is made up of the main stem and up to eight (8) or more lateral branches depending on growing schedule followed.

*Natural flowering season.*—Early January. Flowering time under controlled daylength at 20° C. is 10 weeks in summer and 11½ weeks in winter. Flowering time depends on temperature, light intensity and other growing conditions.

*Flower buds.*—Oblong, up to 6 mm long before showing color, developing to tubular as flower petals mature; sheathed in four (4) yellow green sepals.

*Flowers borne.*—Compound dichasial cyme with primary peduncle being 4 mm in diameter just below the first branch of the inflorescence; length of peduncle will vary depending on growing conditions. Pedicels vary in length depending on where they are in the inflorescence.

*Quantity of flowers.*—Numerous flowers as the maine stem and the eight (8) or more lateral branches will have 50 or more flowers each.

*Petals.*—Shape: Almost rounded, top cuspidate. Color: Top side when opening 53B to 53C, fading to 67B, under side 54A, fading to 67C. Number of petals: Four (4). Size: Individual petals are 5 mm wide and 7 mm long; the flower is approximately 15 mm in diameter.

*Reproductive organs.*—Stamens: Eight (8) in number. Anthers: Flat, elliptical in shape, color yellow-green. Filament color: Yellow-green. Pollen Color: Yellow. Pistils: Stigma: Flat in shape, mature color is white. Style Color: Light green. Ovaries: Four (4) in number, size 5 mm, color green.

Disease resistance: Empress has shown resistance to powdery mildew. No other disease problems have been observed.

Other important characteristics: Empress is an addition to a series of kalanchoe cultivars including Majestic (U.S. Pat. No. P.P. 7,794), Revelry (U.S. Pat. No. P.P. 7,795), Keepsake (U.S. Pat. No. P.P. 7,798), Heirloom (U.S. Pat. No. P.P. 7,810), Legacy, and the cultivars Merit and Chivalry which are disclosed in pending applications. All of these cultivars are matched closely for flowering time, plant height, branching and growth regular response. This allows the domestic greenhouse grower to sell all eight (8) colors at the same time from a single planting date and use the same growing methods on each to end up with a uniform crop. The end result is an easier crop for the grower to produce and a higher quality crop for the consumer to buy. All cultivars are ideal for either 10 or 15 cm pot production.

It is claimed:

1. A new and distinct cultivar of Kalanchoe plant named Empress, as illustrated and described.

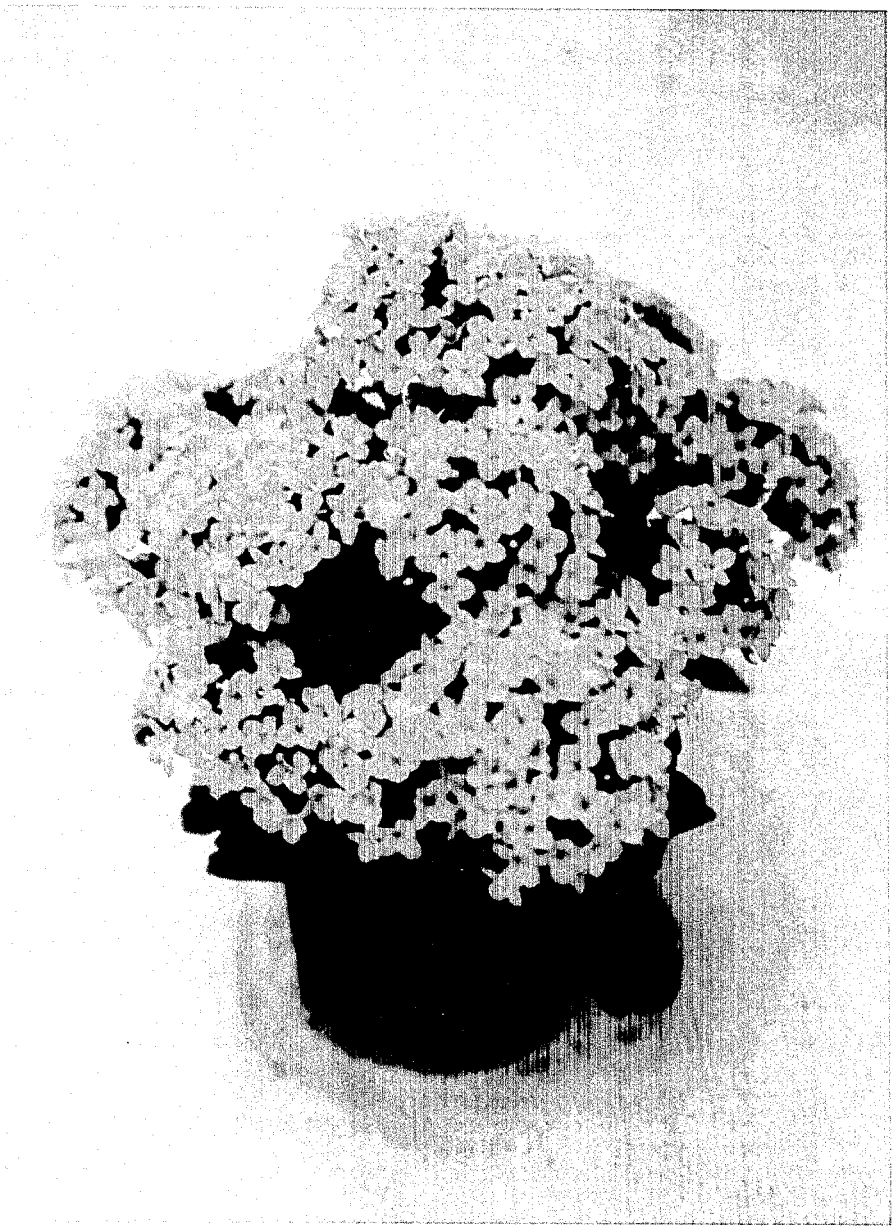

* * * * *